United States Patent
Qu et al.

(10) Patent No.: US 10,514,130 B2
(45) Date of Patent: Dec. 24, 2019

(54) TUBE ARRAY TYPE NITROGEN CANISTER

(71) Applicant: SHANGHAI ORIGINCELL MEDICAL TECHNOLOGY CO., LTD., Shanghai (CN)

(72) Inventors: Jianguo Qu, Shanghai (CN); Chen Luo, Shanghai (CN); Jun Gu, Shanghai (CN)

(73) Assignee: SHANGHAI ORIGINCELL MEDICAL TECHNOLOGY CO., LTD., Pudong District, Shanghai (CN)

( * ) Notice: Subject to any disclaimer, the term of this patent is extended or adjusted under 35 U.S.C. 154(b) by 109 days.

(21) Appl. No.: 15/811,161

(22) Filed: Nov. 13, 2017

(65) Prior Publication Data

US 2018/0135806 A1 May 17, 2018

(30) Foreign Application Priority Data

Nov. 14, 2016 (CN) .......................... 2016 1 1026500

(51) Int. Cl.
*F17C 13/00* (2006.01)
*F17C 13/02* (2006.01)
(Continued)

(52) U.S. Cl.
CPC .............. *F17C 13/001* (2013.01); *A01N 1/00* (2013.01); *A01N 1/0257* (2013.01); *F17C 7/02* (2013.01); *F17C 13/02* (2013.01); *F17C 13/06* (2013.01); *F17C 2201/0119* (2013.01); *F17C 2203/0391* (2013.01); *F17C 2205/0361* (2013.01);
(Continued)

(58) Field of Classification Search
CPC .......... F17C 13/001; F17C 7/02; F17C 13/02; F17C 13/06; F17C 2270/0509; F17C 2201/0119; F17C 2250/0478; F17C 2203/0391; F17C 2205/0361; F17C 2221/014; A01N 1/0257; A01N 1/00; A01J 1/00
See application file for complete search history.

(56) References Cited

U.S. PATENT DOCUMENTS 4,627,595 A * 12/1986 Rhodes .................... F25C 1/243
220/506
5,069,336 A * 12/1991 Mauthe ................. E21D 20/026
206/219
(Continued)

*Primary Examiner* — Kareen K Thomas
(74) *Attorney, Agent, or Firm* — Ping Wang; Morris, Manning & Martin, LLP

(57) ABSTRACT

A tube-array-type liquid nitrogen container includes a container body having a mouth; a tube array component received in the container body; and a top cap sealing the mouth from above. The top cap is rotatable in the mouth. The tube array component is composed of a plurality of holding tubes. The holding tube is opened at one end thereof, wherein the opening thereof faces the top cap. The top cap has at least one tube access passing therethrough. Each tube access is atop covered by a tube access cover. The tube-array-type liquid nitrogen container uses a tube-array component composed of the a plurality of holding tubes to store the freezing tubes, and is cooperated with the rotatable top cap and an external robotic arm, thereby improving space utilization and thermal insulation, effectively ensuring safety of the freezing tubes, and facilitating automatic storage of freezing tubes.

15 Claims, 5 Drawing Sheets

(51) Int. Cl.
  *F17C 13/06* (2006.01)
  *F17C 7/02* (2006.01)
  *A01N 1/00* (2006.01)
  *A01N 1/02* (2006.01)

(52) U.S. Cl.
  CPC ............... *F17C 2221/014* (2013.01); *F17C 2250/0478* (2013.01); *F17C 2270/0509* (2013.01)

(56) References Cited

U.S. PATENT DOCUMENTS

| | | | | |
|---|---|---|---|---|
| 5,370,258 A | * | 12/1994 | Fair | A47G 19/2211 220/501 |
| 5,967,315 A | * | 10/1999 | Langtry, II | A01K 97/06 206/315.11 |
| 6,820,767 B2 | * | 11/2004 | Nicholas | A47G 19/2205 222/132 |
| 6,875,405 B1 | * | 4/2005 | Mathus | B01L 9/06 206/446 |
| 9,181,015 B2 | * | 11/2015 | Booska | B65D 81/3484 |
| 9,718,582 B2 | * | 8/2017 | Hylton | A47G 19/2205 |
| 2005/0236346 A1 | * | 10/2005 | Whitney | B01L 9/06 211/74 |

* cited by examiner

TUBE ARRAY TYPE NITROGEN CANISTER

BACKGROUND OF THE INVENTION

1. Technical Field

The present invention relates to a tube-array-type liquid nitrogen container.

2. Description of Related Art

Liquid nitrogen containers are extensively used in hospitals and laboratories, mainly for freezing and storing biological materials such as cells and tissues. A traditional liquid nitrogen container typically is a double-layer vacuum container that is made by soldering. Such a container has eccentrically an opening and internally a rotatable inner rotator. The inner rotator carries a basket, in which freezing tubes are loaded. Since soldering of such a large device unavoidably has some deformation, accurate rotation of the inner rotator is hard to achieve, in turn making automatic storage of freezing tubes impossible.

SUMMARY OF THE INVENTION

For solving the problem of existing liquid nitrogen containers that automatic storage of freezing tubes is impossible, the present invention provides a tube-array-type liquid nitrogen container.

According to the present invention, a tube-array-type liquid nitrogen container comprises a container body that has a mouth; a tube array component that is received in the container body; and a top cap that seals the mouth from above. The top cap is rotatable in the mouth. The tube array component includes a plurality of holding tubes each configured to hold a freezing tube. The holding tube is opened at one end thereof, wherein the opening faces the top cap. The top cap has at least one tube access passing therethrough, and each tube access is atop covered by a tube access cover. The tube-array-type liquid nitrogen container uses a tube-array component composed of a plurality of holding tubes to store freezing tubes, and with the cooperation of the top cap and the external robotic arm, it realizes automatic access of freezing tubes.

Preferably, the container body has a double-layer structure with a vacuum zone sandwiched between its two layers. Since the intermediate space of the container body is applied with vacuum to form the vacuum zone that provides thermal insulation to the interior of the container body.

Preferably, the container body comprises an inner column and an outer column sleeved outside the inner column. The inner column and the outer column are fixed to each other at bottom. The inner column has its top lower than the top of the outer column. The inner column and the outer column have their tops connected through a corrugated pipe. The corrugated pipe has a wall thickness much smaller than the thickness of the inner column, and meanwhile the stroke is increased by more than one time, so as to reduce heat transmitted to the bottom of the inner column, thereby reducing loss of the liquid nitrogen.

Further preferably, the container body further comprises a sleeve for the corrugated pipe. The sleeve for the corrugated pipe comprises a sleeve end fixed to the top of the outer column and a sleeve body extending downward from the sleeve end. The sleeve body is located inside the corrugated pipe. The sleeve body has its outer periphery that faces the corrugated pipe fitted with the inner periphery of the corrugated pipe, and the sleeve body has its lower end portion fixed to the inner column. The sleeve for the corrugated pipe prevents the inner column deformation caused by corrugated pipe being lengthened.

Further preferably, the inner periphery of the sleeve body is axially sloped and is fitted with the top cap in a sealing manner. The sleeve body with the sloped inner periphery can fit with top cap in a sealing manner better.

Preferably, tube array component further comprises an upper positioning plate, a lower positioning plate, and a central axle that fixedly connects the upper positioning plate and the lower positioning plate. The upper positioning plate is provided with a plurality of upper positioning holes, and the lower positioning plate is provided with a plurality of lower positioning holes. Each of the upper positioning holes is coaxially aligned with one of the lower positioning holes. The holding tube passes through the upper positioning hole and gets positioned in the corresponding lower positioning hole.

Preferably, an auxiliary ball is arranged at the bottom of the holding tube, and the freezing tube is rested on the auxiliary ball. In addition to pushing the freezing tube during the tube-drawing operation, the auxiliary ball also provides damping function when the freezing tube moves downward in the holding tube.

Preferably, the top cap is provided with at least one position sensor. The position sensors may be arranged in circumferential direction of the top cap. The position sensors detect the rotation angle of the top cap, so as to ensure that the top cap rotates accurately.

Preferably, the tube access covers the entire area in radial direction of the tube array component. No matter where the access site of the freezing tube is in the tube array component, the tube access can be aligned to the tube access site by simply rotating the top cap for a certain angle.

Preferably, the tube access cover comprises a roof for the tube access cover and a insulating layer for the tube access cover, wherein the insulating layer is located below the roof, and the insulating layer is fitted with the tube access in a sealing manner. With the insulating layer for the tube access cover and the tube access fitting with each other in a sealing manner, good thermal insulation can be achieved at the tube access.

Based on the common sense in this art, the preferred terms can be combined in various ways to present various embodiments of the present invention.

The present invention provides the following positive advancements:

The tube-array-type liquid nitrogen container uses a tube-array component composed of a plurality of holding tubes to store the freezing tubes, and is cooperated with the rotatable top cap and an external robotic arm, thereby improving space utilization and thermal insulation, effectively ensuring safety of the freezing tubes, and facilitating automatic storage of freezing tubes.

Figure 1:
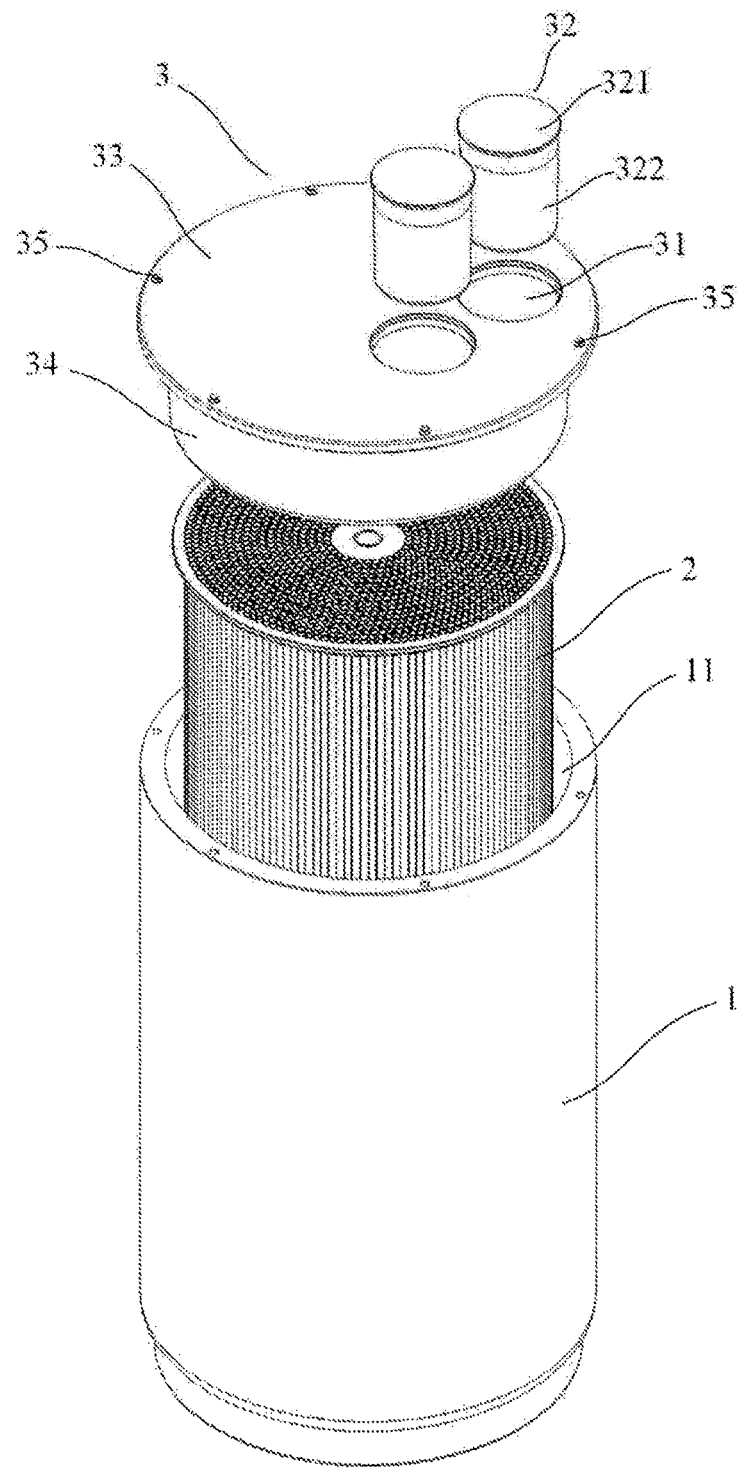
FIG. 1 is an exploded view of a tube-array-type liquid nitrogen container of the present invention.

REFERENCE NUMBERS 1 container body
11 mouth
12 outer column
13 inner column
14 corrugated pipe
15 sleeve for corrugated pipe
151 sleeve end
152 sleeve body
2 tube array component
21 holding tube
22 upper positioning plate
23 lower positioning plate
24 central axle
25 auxiliary ball
3 top cap
31 tube access
32 tube access cover
321 roof for the tube access cover
322 insulating layer for the tube access cover
33 top cap roof
34 top cap insulating layer
35 position sensor
4 freezing tube

DETAILED DESCRIPTION OF THE INVENTION

The following preferred embodiments are made to clearly exhibit the above-mentioned and other technical contents, features and effects of the present invention. However, they are not intended to limit the present invention in any way.

As shown in FIG. 1 to FIG. 5, the present invention provides a tube-array-type liquid nitrogen container. It comprises a container body 1 that has a mouth 11; a tube array component 2 that is received in the container body 1; and a top cap 3 that seals the mouth 11 from above. The top cap 3 is rotatable in the mouth 11. The tube array component 2 comprises a plurality of holding tubes 21 each configured to hold a freezing tube 4. The holding tube 21 is opened at one end thereof, wherein the opening of the holding tube 21 faces the top cap 3. The top cap 3 has at least one tube access 31, which tube access passes through the top cap 3. On the top, the tube access 31 is covered by a tube access cover 32.

The tube-array-type liquid nitrogen container is configured to work with an external robotic arm for automatic access of the freezing tubes through the following process.

To extract a freezing tube 4 (also called freezing storage tube), the external robotic arm rotates the top cap 3 first such that the tube access 31 of the top cap 3 is moved to a targeted site (i.e. a place above the holding tube 21 that holds the targeted freezing tube 4), and then lifts the tube access cover 32 to open the tube access 31. At last, the robotic arm activates and moves its tube-drawing head toward the tube array component 2 from above, so as to form an upward drawing force in the holding tube 21 that holds the targeted freezing tube 4, and draw the freezing tube 4 from above until the freezing tube 4 enters the tube-drawing head.

To store a freezing tube, the external robotic arm first rotates the top cap 3 such that the tube access 31 of the top cap 3 is moved to a targeted site (i.e. a place above the holding tube 21 that is going to receive the freezing tube 4), and then lifts the tube access cover 32 to open the tube access 31. At last, the robotic arm places the freezing tube 4 to be stored into the holding tube 21.

The tube-array-type liquid nitrogen container uses a tube-array component 2 composed of a plurality of holding tubes 21 to store freezing tubes 4, and with the cooperation of the top cap 3 and the external robotic arm, it realizes automatic access of freezing tubes 4.

Figure 2:
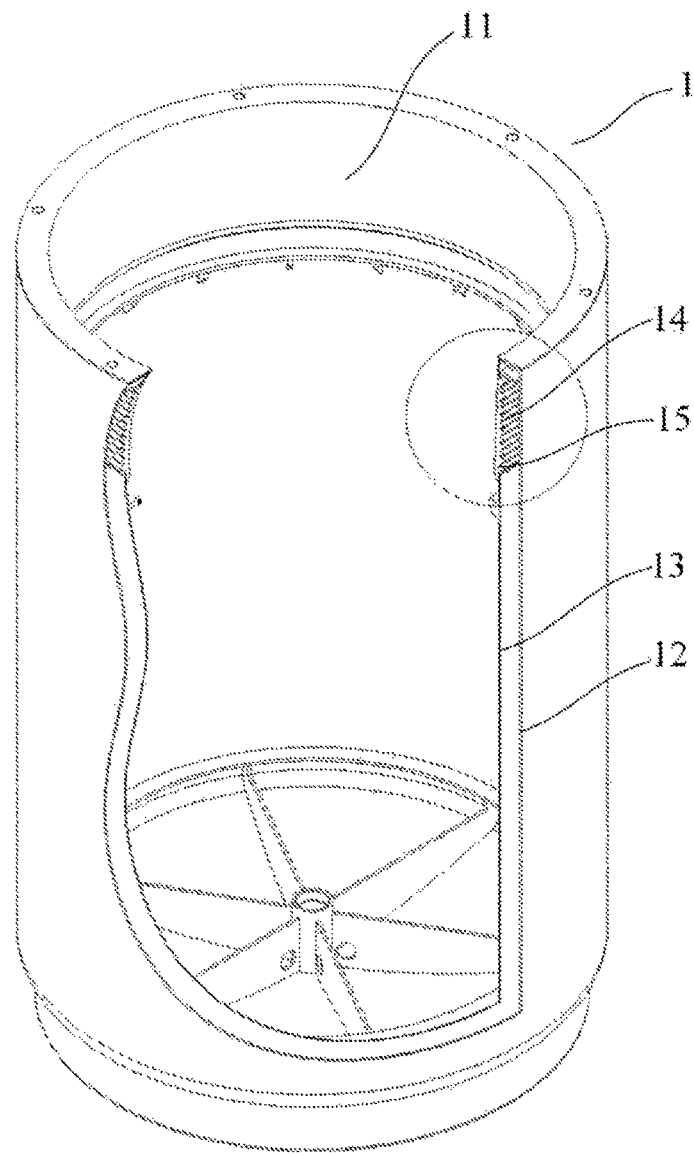
FIG. 2 is a structural drawing of the container body of the tube-array-type liquid nitrogen container of FIG. 1.
Figure 3:
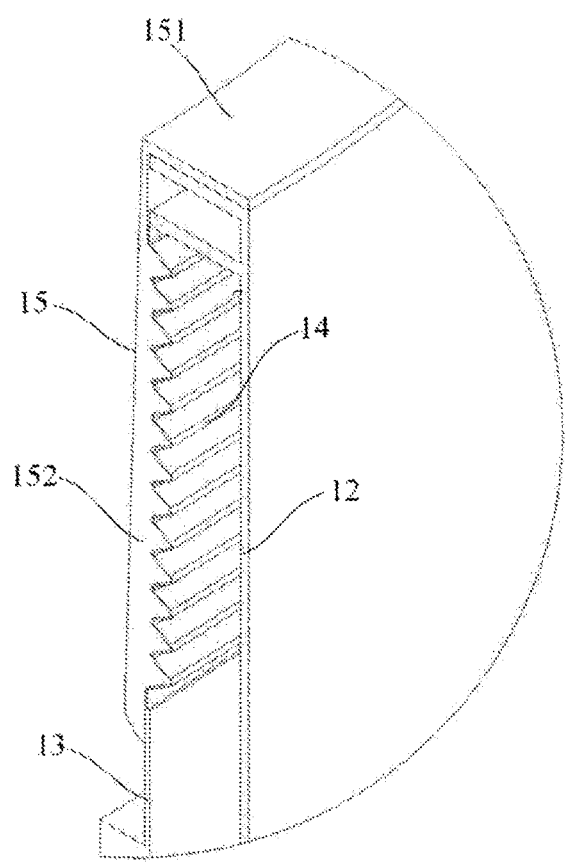
FIG. 3 is a partial enlarged view of the container body of FIG. 2.

As shown in FIG. 2 and FIG. 3, the container body 1 has a double-layer structure with a vacuum zone sandwiched between its two layers. The intermediate space of the container body 1 is applied with vacuum to form a vacuum zone, which provides thermal insulation to the interior of the container body 1.

In one embodiment, the container body 1 has the following configuration. The container body 1 comprises an outer column 12 and an inner column 13, which is enclosed by the outer column 12 at outside. The inner column 13 and the outer column 12 are fixed to each other at bottom. The inner column 13 has its top lower than the top of the outer column 12. The inner column 13 and the outer column 12 have their tops connected through a corrugated pipe 14. The corrugated pipe 14 has a wall thickness much smaller than the thickness of the inner column 13, and meanwhile the pathway is increased by more than one time, so as to reduce heat transmitted to the bottom of the inner column 13, thereby reducing loss of the liquid nitrogen.

The vacuum zone applies a downward pressure to the inner column 13. For preventing the deformation of the inner column 13 caused by corrugated pipe 14 from being lengthened, a sleeve 15 for the corrugated pipe precisely fitting the corrugation profile of the corrugated pipe 14 is sleeved on the corrugated pipe 14. The sleeve 15 for the corrugated pipe is made of a non-metal material that has low thermal conductivity.

The sleeve 15 for the corrugated pipe is configured as below.

The sleeve 15 for the corrugated pipe comprises a sleeve end 151 fixed to the top of the outer column 12 and a sleeve body 152 extending downward from the sleeve end 151. The sleeve body 152 is located inside the corrugated pipe 14. The outer periphery of the sleeve body 152 that faces the corrugated pipe 14, is fitted with the inner periphery of the corrugated pipe 14. The sleeve body 152 has its lower end portion fixed to the inner column 13.

The inner periphery of the sleeve body 152 is such axially sloped that the inner periphery of the sleeve body 152 and the top cap 3 are fitted with each other in a sealing manner. Therein, the top cap 3 comprises a top cap roof 33 and a top cap insulating layer 34 located below the top cap roof 33. The inner periphery of the sleeve body 152 and the outer periphery of the top cap insulating layer 34 are fitted with each other in a sealing manner.

Figure 4:
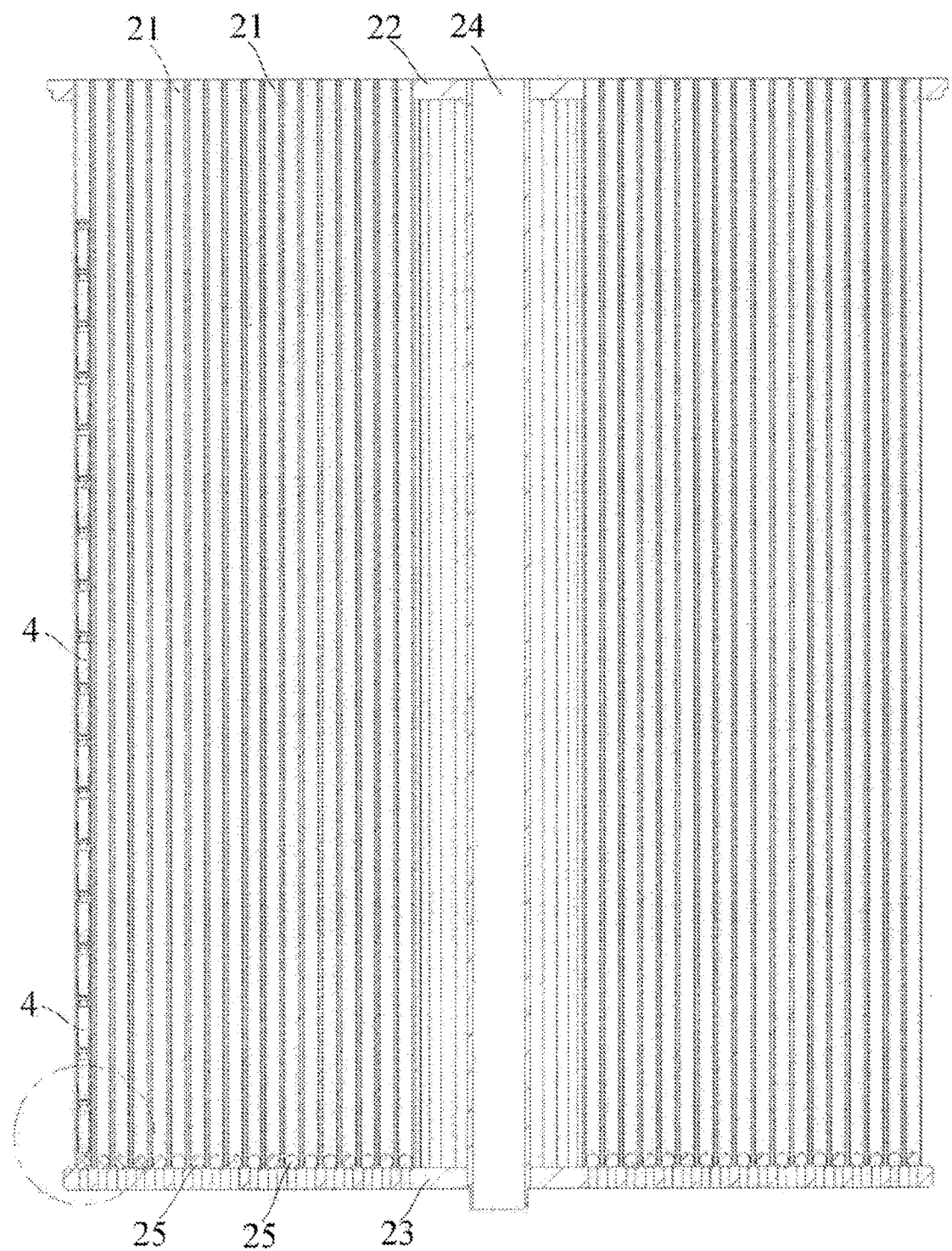
FIG. 4 is a structural schematic drawing of the tube-array component of the tube-array-type liquid nitrogen container of FIG. 1.
Figure 5:
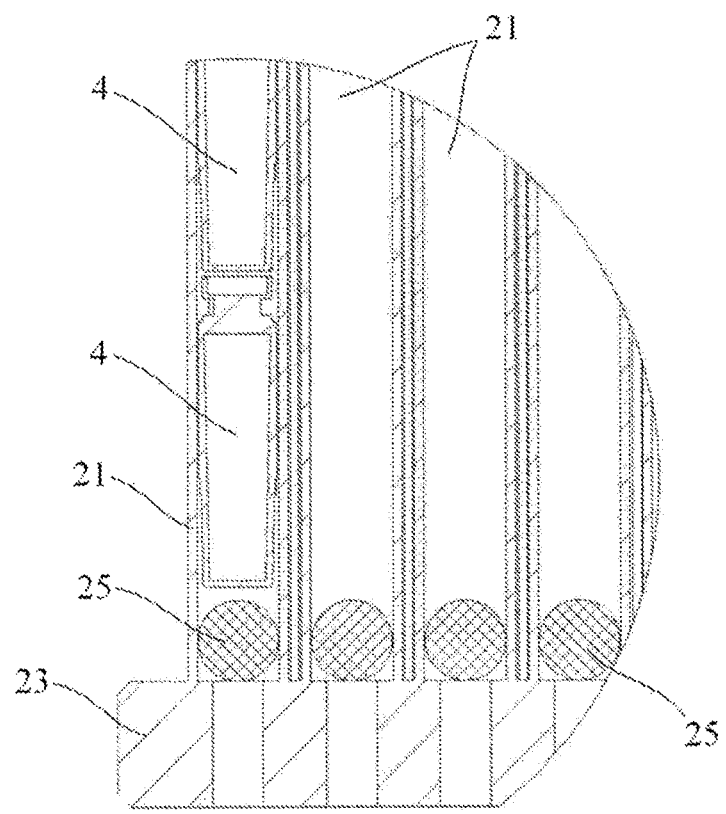
FIG. 5 is a partial enlarged view of the tube-array component of FIG. 4.

As shown in FIG. 4 and FIG. 5, the tube array component 2 further comprises an upper positioning plate 22, a lower positioning plate 23, and a central axle 24 that fastens the upper positioning plate 22 and the lower positioning plate 23. The upper positioning plate 22 is provided with a plurality of upper positioning holes, and the lower positioning plate 23 is provided with a plurality of lower positioning holes. Each of the upper positioning holes is coaxially aligned with one of the lower positioning holes. The holding tube 21 passes through the upper positioning hole and then gets fixed in the corresponding lower positioning hole. The upper positioning plate 22 and the lower positioning plate 23 are parallel to each other. The upper positioning plate 22 and the lower positioning plate 23 are centrally connected by the central axle 24. The plural upper positioning holes are distributed along the periphery of the central axle 24 in loop by loop manner, while the plural lower positioning holes are also distributed along the periphery of the central axle 24 in loop by loop manner.

An auxiliary ball 25 is arranged at the bottom of the holding tube 21, so that the freezing tube 4 can be rested on the auxiliary ball 25. The auxiliary ball 25 has a diameter slightly smaller than that of the holding tube 21, and is made of a relatively soft and lightweight material, such as silicone. When the tube-drawing head of the robotic arm draws the freezing tube 4 upward, the auxiliary ball 25 will be also sucked and moved upward, thereby pushing the freezing tube 4 above it to move upward. In addition to pushing the freezing tube 4 during the tube-drawing operation, the auxiliary ball 25 also functions for damping the freezing tube 4 when the freezing tube 4 falls down into the holding tube 21.

The top cap 3 is provided with at least one position sensor 35. The position sensors 35 may be arranged in circumferential direction of the top cap 3. Before the accessing operation, a position of a freezing tube 4 to be accessed is first detected. Then the robotic arm rotates and moves the top cap 3 to a predetermined site. During rotation, the position sensor 35 detects the rotation angle of the top cap 3, so as to ensure that the top cap 3 rotates into a proper position. In an embodiment where plural position sensors 35 are arranged in circumferential direction of the top cap 3, wherein preferred that the top cap 3 is peripherally provided with six evenly distributed position sensors 35.

The tube access 31 covers the entire area in radial direction of the tube array component 2. No matter where the access site of the freezing tube 4 is in the tube array component 2, the tube access 31 can be aligned to the access site by simply rotating the top cap 3 for a certain angle, thereby realizing full coverage to all the access sites in the tube array component 2. For minimizing the area of the tube access 31 while providing full coverage, there may be a plurality of tube accesses 31 arranged at different positions in radial direction of the tube array component 2. Preferably, as shown in FIG. 1, there are two tube accesses 31. The minimized area of the tube access 31 helps to minimize loss of liquid nitrogen when the tube access 31 is open.

As shown in FIG. 1, the tube access cover 32 comprises a roof 321 for the tube access cover and a insulating layer 322 for the tube access cover, which insulating layer is located below the roof 321. The insulating layer 322 and the tube access 31 are fitted with each other in a sealing manner.

The holding tube 21 is usually an aluminum tube, and has a length such designed that the holding tube 21 is several times as long as the length of the freezing tube 4, so that a plurality of freezing tubes 4 can be put into the holding tube 21 successively.

To sum up, the tube-array-type liquid nitrogen container of the present invention uses the tube-array component composed of a plurality of holding tubes to store the freezing tubes, and is cooperated with the rotatable top cap and an external robotic arm, thereby improving space utilization and thermal insulation, effectively ensuring safety of the freezing tubes, and facilitating automatic storage of freezing tubes.

The present invention has been described with reference to the preferred embodiments and it is understood that the embodiments are not intended to limit the scope of the present invention. Moreover, as the contents disclosed herein should be readily understood and can be implemented by a person skilled in the art, all equivalent changes or modifications which do not depart from the concept of the present invention should be encompassed by the appended claims.

What is claimed is:

1. A tube-array-type liquid nitrogen container, comprising a container body (1) with a mouth (11); a tube array component (2) received in the container body (1); and a top cap (3) sealing the mouth (11) from above;
    wherein the top cap (3) is rotatably arranged in the mouth (11),
    wherein the tube array component (2) includes a plurality of holding tubes (21) each configured to hold a freezing tube (4), the holding tubes (21) are such opened at one end thereof that the openings of the holding tubes (21) face the top cap (3), the top cap (3) has at least one tube access (31) passing through the top cap (3), and the at least one tube access (31) is covered by a tube access cover (32) on the top, and
    wherein the container body (1) comprises an inner column (13) and an outer column (12) sleeving the inner column (13) at an outside, wherein the inner column (13) and the outer column (12) are fixed to each other at a bottom, the inner column (13) has its top lower than a top of the outer column (12), and the top of the inner column (13) and the top of the outer column (12) are connected through a corrugated pipe (14).

2. The tube-array-type liquid nitrogen container of claim 1, wherein the container body (1) has a double-layer structure with a vacuum zone sandwiched between its two layers.

3. The tube-array-type liquid nitrogen container of claim 1, wherein the container body (1) further comprises a sleeve (15) for the corrugated pipe with a sleeve end (151) fixed to the top of the outer column (12) and with a sleeve body (152) extending downward from the sleeve end (151), wherein the sleeve body (152) is located inside the corrugated pipe (14), the sleeve body (152) has its outer periphery that faces the corrugated pipe (14) fitted with an inner periphery of the corrugated pipe (14), and the sleeve body (152) has a lower end portion thereof fixed to the inner column (13).

4. The tube-array-type liquid nitrogen container of claim 3, wherein an inner periphery of the sleeve body (152) is axially sloped, and fitted with the top cap (3) in a sealing manner.

5. The tube-array-type liquid nitrogen container of claim 1, wherein the tube array component (2) further comprises an upper positioning plate (22), a lower positioning plate (23), and a central axle (24) fixedly connecting the upper positioning plate (22) and lower positioning plate (23), wherein the upper positioning plate (22) is provided with a plurality of upper positioning holes, the lower positioning plate (23) is provided with a plurality of lower positioning holes, and each of the plurality of upper positioning holes is coaxially aligned with one of the plurality of lower positioning holes, so that the holding tube (21) passing through each of the plurality of upper positioning holes can be positioned in its corresponding lower positioning hole.

6. The tube-array-type liquid nitrogen container of claim 1, wherein the tube access (31) covers an entire area in radial direction of the tube array component (2).

7. The tube-array-type liquid nitrogen container of claim 1, wherein the tube access cover (32) comprises a roof (321) for the tube access cover and an insulating layer (322) for the tube access cover, wherein the insulating layer is located below the roof (321), and the insulating layer (322) is fitted with the tube access (31) in a sealing manner.

8. The tube-array-type liquid nitrogen container of claim 2, wherein the container body (1) comprises an inner column

(13) and an outer column (12) sleeving the inner column (13) at outside, wherein the inner column (13) and the outer column (12) are fixed to each other at bottom, the inner column (13) has its top lower than a top of the outer column (12), and the top of the inner column (13) and the top of the outer column (12) are connected through a corrugated pipe (14).

9. The tube-array-type liquid nitrogen container of claim 8, wherein the container body (1) further comprises a sleeve (15) for the corrugated pipe with a sleeve end (151) fixed to the top of the outer column (12) and with a sleeve body (152) extending downward from the sleeve end (151), wherein the sleeve body (152) is located inside the corrugated pipe (14), the sleeve body (152) has its outer periphery that faces the corrugated pipe (14) fitted with an inner periphery of the corrugated pipe (14), and the sleeve body (152) has a lower end portion thereof fixed to the inner column (13).

10. The tube-array-type liquid nitrogen container of claim 9, wherein an inner periphery of the sleeve body (152) is axially sloped, and fitted with the top cap (3) in a sealing manner.

11. The tube-array-type liquid nitrogen container of claim 5, wherein an auxiliary ball (25) is arranged at a bottom of the holding tube (21), and the freezing tube (4) is rested on the auxiliary ball (25).

12. A tube-array-type liquid nitrogen container, comprising a container body (1) with a mouth (11); a tube array component (2) received in the container body (1); and a top cap (3) sealing the mouth (11) from above;
    wherein the top cap (3) is rotatably arranged in the mouth (11),
    wherein the tube array component (2) includes a plurality of holding tubes (21) each configured to hold a freezing tube (4), the holding tubes (21) are such opened at one end thereof that the openings of the holding tubes (21) face the top cap (3), the top cap (3) has at least one tube access (31) passing through the top cap (3), and the at least one tube access (31) is covered by a tube access cover (32) on the top, and
    wherein an auxiliary ball (25) is arranged at a bottom of the holding tube (21), and the freezing tube (4) is rested on the auxiliary ball (25).

13. A tube-array-type liquid nitrogen container, comprising a container body (1) with a mouth (11); a tube array component (2) received in the container body (1); and a top cap (3) sealing the mouth (11) from above;
    wherein the top cap (3) is rotatably arranged in the mouth (11),
    wherein the tube array component (2) includes a plurality of holding tubes (21) each configured to hold a freezing tube (4), the holding tubes (21) are such opened at one end thereof that the openings of the holding tubes (21) face the top cap (3), the top cap (3) has at least one tube access (31) passing through the top cap (3), and the at least one tube access (31) is covered by a tube access cover (32) on the top, and
    wherein the top cap (3) is provided with at least one position sensor (35) being arranged in circumferential direction of the top cap (3).

14. A tube-array-type liquid nitrogen container, comprising a container body (1) with a mouth (11); a tube array component (2) received in the container body (1); and a top cap (3) sealing the mouth (11) from above; the tube array component (2) includes a plurality of holding tubes (21) each configured to hold a freezing tube (4), the holding tubes (21) are such opened at one end thereof that the openings of the holding tubes (21) face the top cap (3); an auxiliary ball (25) is arranged at a bottom of one of the holding tubes (21), the freezing tube (4) is rested on the auxiliary ball (25), and the diameter of the auxiliary ball (25) is smaller than the diameter of the one of the holding tubes (21).

15. A tube-array-type liquid nitrogen container, comprising a container body (1) with a mouth (11); a tube array component (2) received in the container body (1); and a top cap (3) sealing the mouth (11) from above; the container body (1) comprises an inner column (13) and an outer column (12) sleeving the inner column (13) at outside, wherein the inner column (13) and the outer column (12) are fixed to each other at bottom, and the top of the inner column (13) and the top of the outer column (12) are connected through a corrugated pipe (14); the container body (1) further comprises a sleeve (15) for the corrugated pipe (14) with a sleeve end (151) fixed to the top of the outer column (12) and with a sleeve body (152) extending downward from the sleeve end (151), wherein the sleeve body (152) is located inside the corrugated pipe (14), the sleeve body (152) has its outer periphery that faces the corrugated pipe (14) fitted with an inner periphery of the corrugated pipe (14), and the sleeve body (152) has a lower end portion thereof fixed to the inner column (13).

* * * * *